United States Patent
Kassab et al.

(10) Patent No.: US 10,835,285 B2
(45) Date of Patent: *Nov. 17, 2020

(54) DEVICES, SYSTEMS, AND METHODS FOR DELIVERING A SUBSTANCE WITHIN A MAMMALIAN LUMINAL ORGAN OR AREA ADJACENT THERETO

(71) Applicant: CVDevices, LLC, San Diego, CA (US)

(72) Inventors: Ghassan S. Kassab, La Jolla, CA (US); Jose A. Navia, Sr., Buenos Aires (AR)

(73) Assignee: CVDevices, LLC, San Diego, CA (US)

( * ) Notice: Subject to any disclaimer, the term of this patent is extended or adjusted under 35 U.S.C. 154(b) by 309 days.

This patent is subject to a terminal disclaimer.

(21) Appl. No.: 15/877,739

(22) Filed: Jan. 23, 2018

(65) Prior Publication Data

US 2018/0146984 A1 May 31, 2018

Related U.S. Application Data

(63) Continuation of application No. 14/416,689, filed as application No. PCT/US2013/051545 on Jul. 22, 2013, now Pat. No. 9,872,704.
(Continued)

(51) Int. Cl.
*A61B 17/34* (2006.01)
*A61M 25/06* (2006.01)
(Continued)

(52) U.S. Cl.
CPC ..... *A61B 17/3478* (2013.01); *A61M 25/0662* (2013.01); *A61B 2017/00247* (2013.01);
(Continued)

(58) Field of Classification Search
CPC . A61B 18/1492; A61B 17/0057; A61B 17/22; A61B 17/3478; A61M 25/104;
(Continued)

(56) References Cited

U.S. PATENT DOCUMENTS 2,512,569 A * 6/1950 Saffir ................ A61M 5/32
604/272
5,167,624 A 12/1992 Butler et al.
(Continued)

OTHER PUBLICATIONS

International Searching Authority, International Search Report, PCT/US2013/151545, dated Dec. 20, 2013.
(Continued)

*Primary Examiner* — Manuel A Mendez
(74) *Attorney, Agent, or Firm* — Reichel Stohry Dean LLP; Mark C. Reichel; Natalie J. Dean

(57) ABSTRACT

Devices, systems, and methods for delivering a substance within a mammalian luminal organ or area adjacent thereto. In at least one exemplary embodiment of a system of the present disclosure, the system comprises an inner delivery device, comprising an inner portion configured to receive a substance therein, a pock tip at or near a distal end of the inner delivery device, the pock tip configured to deliver the substance from the inner portion, through a pock tip aperture defined within the pock tip, and into a mammalian tissue and/or luminal organ, and an embolus positioned within the inner portion, the embolus configured so that the substance remains distal to the embolus when the substance is positioned within the inner portion. In another embodiment, the system further comprises an outer catheter, comprising an elongate body, a guidewire lumen defined within the elongate body and configured to receive at least part of a guidewire therein, and a central lumen defined within the elongate body, the central lumen configured to receive at least a portion of the inner delivery device.

19 Claims, 7 Drawing Sheets

Related U.S. Application Data

(60) Provisional application No. 61/674,589, filed on Jul. 23, 2012.

(51) Int. Cl.
*A61B 17/00* (2006.01)
*A61B 17/22* (2006.01)
*A61B 17/30* (2006.01)

(52) U.S. Cl.
CPC ............ *A61B 2017/22038* (2013.01); *A61B 2017/22055* (2013.01); *A61B 2017/22069* (2013.01); *A61B 2017/306* (2013.01); *A61M 2025/0681* (2013.01); *A61M 2210/125* (2013.01)

(58) Field of Classification Search
CPC .............. A61M 25/10; A61M 25/1002; A61M 25/1011; A61M 25/0084; A61F 2/958; A61F 2/966; A61F 2/95
See application file for complete search history.

(56) References Cited

U.S. PATENT DOCUMENTS

| | | | |
|---|---|---|---|
| 6,726,677 B1 * | 4/2004 | Flaherty | A61B 1/3137 |
| | | | 600/439 |
| 9,872,704 B2 * | 1/2018 | Kassab | A61B 17/3478 |
| 2002/0049414 A1 * | 4/2002 | Nobles | A61B 17/22 |
| | | | 604/187 |
| 2010/0094256 A1 | 4/2010 | Kassab | |
| 2011/0060276 A1 | 3/2011 | Schaeffer et al. | |
| 2012/0108926 A1 | 5/2012 | Kassab | |

OTHER PUBLICATIONS

International Searching Authority (ISA), Written Opinion of the ISA, PCT/US2013/0151545, dated Dec. 20, 2013.

* cited by examiner

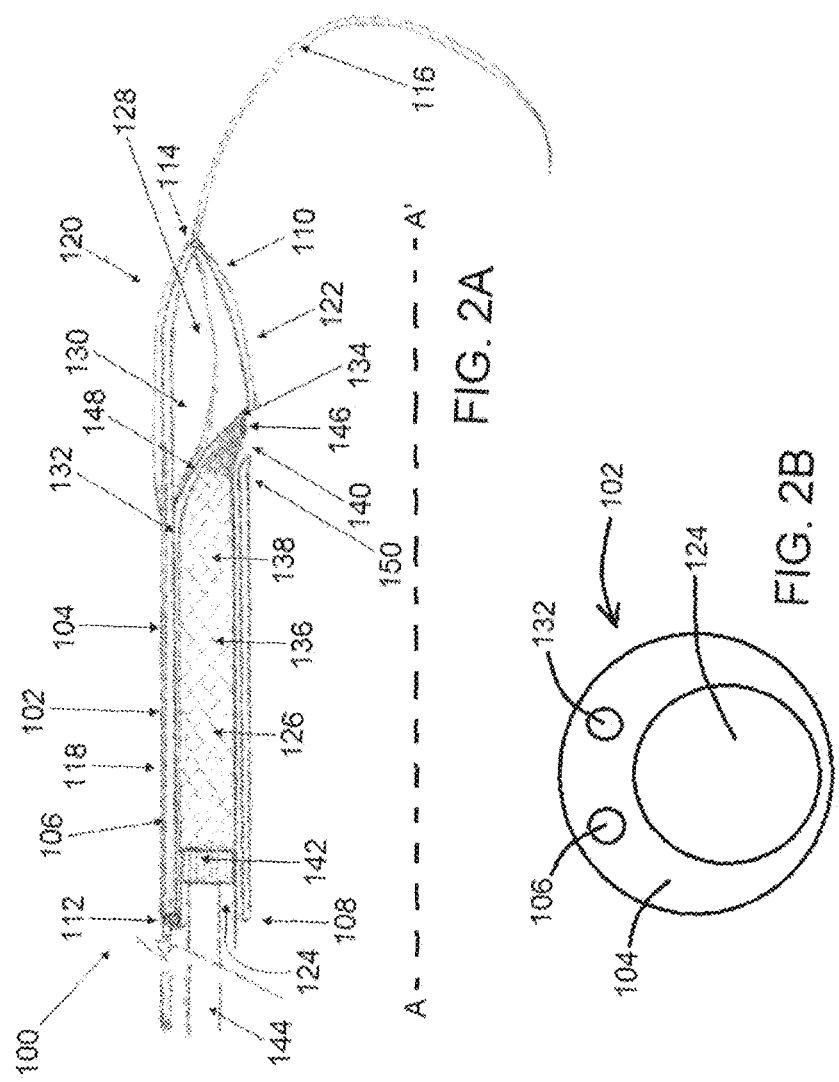

DEVICES, SYSTEMS, AND METHODS FOR DELIVERING A SUBSTANCE WITHIN A MAMMALIAN LUMINAL ORGAN OR AREA ADJACENT THERETO

PRIORITY

The present application is related to, claims the priority benefit of, and is a U.S. continuation patent application of, U.S. patent application Ser. No. 14/416,689, filed Jan. 23, 2015 and issued as U.S. Pat. No. 9,872,704 on Jan. 23, 2018, which is related to, claims the priority benefit of, and is a U.S. national stage (§ 371) patent application of, PCT Patent Application Serial No. PCT/US2013/051545, filed Jul. 22, 2013, which is related to, and claims the priority benefit of, U.S. Provisional Patent Application Ser. No. 61/674,589, filed Jul. 23, 2012. The contents of each of the foregoing patent applications and patent are hereby incorporated by reference in their entirety into this disclosure.

BACKGROUND

Proper delivery of a substance (drug, biopolymer, etc.) to a targeted location within a patient, especially to a targeted location within a luminal organ, is somewhat difficult given the locations of certain tissues and/or organs within the body. For example, should a patient need a specific drug delivered locally within the heart, the physician (a surgeon or interventionalist, for example), would need to determine the best method to do so and which equipment/devices would be most suitable for the procedure.

A system, configured for intravascular insertion into a patient and advancement to a desired location, and further configured to precisely deliver a desired amount of a drug or other substance within the patient, would be well received within the medical arts.

BRIEF SUMMARY

In at least one exemplary embodiment of a system of the present disclosure, the system comprises an inner delivery device, comprising an inner portion configured to receive a substance therein, a pock tip at or near a distal end of the inner delivery device, the pock tip configured to deliver the substance from the inner portion, through a pock tip aperture defined within the pock tip, and into a mammalian tissue and/or luminal organ, and an embolus positioned within the inner portion, the embolus configured so that the substance remains distal to the embolus when the substance is positioned within the inner portion. In another embodiment, the inner delivery device further comprises a delivery shaft positioned proximal to the embolus, the delivery shaft configured to fit within the inner delivery device and facilitate delivery of the substance by way of distal advancement of the embolus within the inner delivery device. In yet another embodiment, the inner delivery device further comprises a needle wire channel defined within the inner delivery device, the needle wire channel configured to receive at least a portion of a needle wire therein. In an additional embodiment, the inner delivery device further comprises the needle wire, wherein at least part of the needle wire is configured to fit within the needle wire channel.

In at least one exemplary embodiment of a system of the present disclosure, the system further comprises a torque mechanism coupled to the inner delivery device at or near a proximal end of the inner delivery device, the torque mechanism comprising a first rotatable dial configured such that rotation of the first rotatable dial in a first direction advances the delivery shaft distally within the inner delivery device. In an additional embodiment, the system further comprises a first limiter coupled to the inner delivery device, the first limiter configured to limit advancement of the delivery shaft within the inner delivery device. In yet an additional embodiment, the inner delivery device is configured to deliver the substance into the mammalian tissue and/or luminal organ or a space adjacent thereto. In another embodiment, the pock tip is configured to puncture the mammalian tissue and/or luminal organ.

In at least one exemplary embodiment of a system of the present disclosure, the inner delivery device is configured to deliver the substance into the mammalian tissue and/or luminal organ or a space adjacent thereto after the pock tip has punctured the mammalian tissue and/or luminal organ. In another embodiment, the inner delivery device is configured to deliver the substance into the mammalian tissue and/or luminal organ or a space adjacent thereto after the pock tip has punctured the mammalian tissue and/or luminal organ by delivering the substance from the inner portion through the pock tip and into the mammalian tissue and/or luminal organ. In yet another embodiment, the system further comprises the substance. In an additional embodiment, the substance is selected from the group consisting of a medicament, a polymer, a growth factor, a cell, a myocardial cell, a biological material, and a combination of one or more of the foregoing.

In at least one exemplary embodiment of a system of the present disclosure, the pock tip comprises a material selected from the group consisting of a biologically-compatible metal and a biologically-compatible plastic/polymer. In additional embodiments, the pock tip is rigid or tapered. In another embodiment, the system further comprises an outer catheter, comprising an elongate body, a guidewire lumen defined within the elongate body and configured to receive at least part of a guidewire therein, and a central lumen defined within the elongate body, the central lumen configured to receive at least a portion of the inner delivery device.

In at least one exemplary embodiment of a system of the present disclosure, the guidewire lumen is configured so that the other catheter may be advanced over the guidewire. In an additional embodiment, the system further comprises the guidewire, wherein at least part of the guidewire is configured to fit within the guidewire lumen. In yet an additional embodiment, the guidewire has a preformed shape. In another embodiment, the preformed shape corresponds to a bodily organ measurement, and wherein the outer catheter may be advanced over the guidewire to a targeted location of the bodily organ. In yet another embodiment, a distal portion of the outer catheter is tapered.

In at least one exemplary embodiment of a system of the present disclosure, the system further comprises a first guidewire having a first preformed shape, and a second guidewire having a second preformed shape, wherein each of the first guidewire and the second guidewire are configured to separately fit within the guidewire lumen. In another embodiment, the guidewire lumen has a smaller cross-sectional area than the central lumen. In another embodiment, the system further comprises an inflation tube, the inflation tube defined within the outer catheter and configured to attach to an inflation source. In an additional embodiment, the system further comprises a first balloon, wherein the inflation tube terminates at the first balloon.

In at least one exemplary embodiment of a system of the present disclosure, the first balloon is positioned within a balloon chamber defined within the outer catheter at or near a distal end of the outer catheter. In an additional embodiment, the first balloon is configured for inflation by way of introduction of an inflation agent from the inflation source, through the inflation tube, and into the first balloon. In yet an additional embodiment, the system further comprises a second balloon, and a third balloon, wherein the second balloon and the third balloon are configured for inflation by way of introduction of the inflation agent from the inflation source, through the inflation tube, and into the second balloon and the third balloon. In another embodiment, inflation of one or more of the first balloon, the second balloon, and/or the third balloon facilitates stabilization of the outer catheter within a mammalian luminal organ.

In at least one exemplary embodiment of a system of the present disclosure, the outer catheter is configured for intravascular insertion into a mammalian patient and advancement to a targeted location within the mammalian patient. In another embodiment, the targeted location is selected from the group consisting of a pericardial sac, is an epicardial surface of a heart, and a myocardium. In yet another embodiment, the outer catheter has at least one open channel defined therein, the at least one open channel configured so that the pock tip can protrude therefrom. In an additional embodiment, the outer catheter has a plurality of open channels defined therein, the plurality of open channels configured so that the pock tip can protrude therefrom at different locations along the outer catheter.

In at least one exemplary embodiment of a system of the present disclosure, the outer catheter further comprises a pock tip wall positioned at or near a distal end of the outer catheter, the pock tip wall configured to facilitate protrusion of the pock tip after the pock tip is advanced distally inside the outer catheter to the pock tip wall. In an additional embodiment, the pock tip wall is tapered toward at least one open channel defined within the outer catheter. In yet an additional embodiment, the pock tip is tapered, and wherein the tapered pock tip corresponds to the tapered pock tip wall. In another embodiment, the system further comprises a suction channel, the suction channel defined within the outer catheter and configured to attach to a suction source.

In at least one exemplary embodiment of a system of the present disclosure, the system further comprises a suction chamber, wherein the suction channel terminates at the suction chamber. In another embodiment, suction from the suction source, through the suction channel and to the suction chamber facilitates stabilization of the outer catheter within a mammalian luminal organ. In yet another embodiment, the guidewire is configured for percutaneous intravascular advancement into a mammalian vasculature, and wherein at least part of the outer catheter is configured for advancement over the guidewire and into the mammalian vasculature. In an additional embodiment, the guidewire lumen extends from a device proximal portion to a device distal portion, and wherein the guidewire lumen defines a proximal opening and a distal opening.

In at least one exemplary embodiment of a system of the present disclosure, the guidewire lumen is defined at or near a relative perimeter of the elongated body. In an additional embodiment, the guidewire lumen is tapered at or near the device distal portion. In yet an additional embodiment, the guidewire lumen is configured to receive a portion of a guidewire through the proximal opening, through the guidewire lumen, and out of the distal opening. In another embodiment, the inner delivery device is configured to deliver the substance into the mammalian tissue and/or luminal organ or a space adjacent thereto while a portion of the outer catheter is reversibly stabilized within the luminal organ or a vasculature adjacent thereto.

In at least one exemplary embodiment of a system of the present disclosure, the system further comprises at least one balloon is positioned within a balloon chamber defined within the outer catheter at or near a distal end of the outer catheter or otherwise coupled to the outer catheter, wherein the outer catheter is reversibly stabilized by way of inflation of the at least one balloon. In another embodiment, inflation of the at least one balloon occurs by delivering a substance through an inflation tube coupled to the at least one balloon into the at least one balloon. In yet another embodiment, the inflation tube is positioned or defined within the outer catheter. In an additional embodiment, the inflation tube is external to the outer catheter. In yet an additional embodiment, the preformed shape includes at least one curvature.

In at least one exemplary embodiment of a system of the present disclosure, the preformed shape of the guidewire corresponds to at least one heart diameter so that advancement of the guidewire out of the outer catheter causes at least part of the guidewire to encircle a heart. In an additional embodiment, the guidewire comprises a material selected from the group consisting of nitinol, chromium, cadmium, molybdenum, nickel, nickel composite, a nickel titanium alloy, a nickel cadmium alloy, a nickel chromium alloy, a nitinol palladium alloy, a palladium cobalt alloy, and platinum. In yet an additional embodiment, the preformed shape remains after delivery of at least a portion of the guidewire through the outer catheter and into a mammalian tissue and/or luminal organ. In another embodiment, the inner delivery device comprises a material selected from the group consisting of a plastic, a polymer, a biologically-compatible material, polyurethane, and Teflon. In yet another embodiment, the outer catheter comprises a material selected from the group consisting of a plastic, a polymer, a biologically-compatible material, polyurethane, and Teflon.

In at least one exemplary embodiment of a system of the present disclosure, the system further comprises at least one balloon is positioned within a balloon chamber defined within the outer catheter at or near a distal end of the outer catheter or otherwise coupled to the outer catheter. In another embodiment, the at least one balloon comprises a balloon group comprising a central compliance balloon, a first lateral balloon, and a second lateral balloon. In yet another embodiment, when the balloon group is configured to minimize stress to a mammalian vasculature when the balloon group is inflated within the mammalian vasculature. In an additional embodiment, at least one of the plurality of open channels comprises an angle relative to a longitudinal axis of the outer catheter, the angle selected from the group consisting of 30°, 40°, 60°, 90°, or an angle greater than 0° and less than 180°.

In at least one exemplary embodiment of a system of the present disclosure, the pock tip wall comprises a configuration selected from the group consisting of a complete wall, one or more internal bars, and one or more internal protrusions. In an additional embodiment, the pock tip and the pock tip wall each comprise a relatively straight taper. In yet an additional embodiment, the pock tip and the pock tip wall each comprise a relatively curved taper. In another embodiment, the system further comprises a handle coupled to the inner delivery device, the handle configured to be held by a user of the inner delivery device during operation of the inner delivery device.

In at least one exemplary embodiment of a system of the present disclosure, the torque mechanism is selected from the group consisting of a manual mechanism, a mechanical mechanism, and a compressed air mechanism. In another embodiment, the torque mechanism further comprises a second rotatable dial configured such that rotation of the second rotatable dial in a first direction advances the inner delivery device within the central lumen of the outer catheter, and such that rotation of the second rotatable dial in a second direction retracts the inner delivery device within the central lumen of the outer catheter.

In at least one exemplary embodiment of a method to deliver a substance within a mammalian patient, the method comprises the steps of introducing at least part of a system into a mammalian patient, the system comprising an inner delivery device and an outer catheter, advancing the at least part of the system within the mammalian patient to a targeted tissue or luminal organ, and advancing at least part of the inner delivery device within the outer catheter of to a first location so to deliver a substance from within the inner delivery device, through a pock tip of the inner delivery device, and into the targeted tissue or luminal organ, wherein the pock tip protrudes from a first open channel defined within the outer catheter. In another embodiment, the step of introducing comprises initially introducing at least part of a guidewire into the mammalian patient and advancing the at least part of the system over the guidewire. In yet another embodiment, the guidewire is preformed corresponding to a measurement of a bodily organ, and wherein the at least part of the system is advanced over the guidewire to a targeted location of the bodily organ. In an additional embodiment, the targeted tissue or luminal organ is selected from the group consisting of a pericardial sac, is an epicardial surface of a heart, and a myocardium. In yet an additional embodiment, the delivery of the substance is facilitated by advancement of an embolus and a delivery shaft within the inner delivery device.

In at least one exemplary embodiment of a method to deliver a substance within a mammalian patient, advancement of the embolus is caused by operation of a torque mechanism coupled to the delivery shaft. In an additional embodiment, rotation of the torque mechanism in a first direction advances the embolus, and whereby rotation of the torque mechanism in a second direction retracts the embolus. In yet an additional embodiment, rotation of the torque mechanism in a defined rotation amount corresponds to a particular incremental advancement of the delivery shaft. In another embodiment, rotation of the torque mechanism in a defined rotation amount corresponds to a particular incremental delivery of the substance into the mammalian patient. In yet another embodiment, advancement of the inner delivery device within the outer catheter is caused by operation of a second torque mechanism coupled to the inner delivery device or the outer catheter.

In at least one exemplary embodiment of a method to deliver a substance within a mammalian patient, the method further comprises the step of moving at least part of the inner delivery device to a second location within the outer catheter so to deliver a substance from within the inner delivery device at the second location, through a pock tip of the inner delivery device, and into the targeted tissue or luminal organ, wherein the pock tip protrudes from a second open channel defined within the outer catheter. In another embodiment, the method further comprises the step of removing the at least part of the system from the patient. In yet another embodiment, the method further comprises the step of stabilizing the outer catheter within the mammalian patient after the step of advancing the at least part of the system within the mammalian patient to the targeted tissue or luminal organ. In an additional embodiment, the step of stabilizing is performed by inflating at least one balloon positioned within a balloon chamber defined within the outer catheter or otherwise coupled to the outer catheter. In yet an additional embodiment, the step of stabilizing is performed by applying suction to one or more suction channels defined within the outer catheter, the one or more suction channels terminating at one or more suction chambers.

In at least one exemplary embodiment of a method to deliver a substance within a mammalian patient, the step of advancing at least part of the inner delivery device within the outer catheter of to a first location so to deliver the substance from within the inner delivery device is performed in connection with puncturing the targeted tissue or luminal organ using the pock tip. In another embodiment, the outer catheter further defines a needle wire channel therein and a needle at least partially positioned within the needle wire channel, and the method further comprises the step of advancing the needle to puncture the targeted tissue or luminal organ to facilitate advancement of the pock tip into the targeted tissue or luminal organ. In yet another embodiment, the method is performed to treat the mammalian patient by delivering the substance to the mammalian patient.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIG. 2A shows a side cut-away view of a catheter system, according to an exemplary embodiment of the present disclosure;

FIG. 2B shows a cross-sectional view of a catheter system, according to an exemplary embodiment of the present disclosure;

Figure 1:
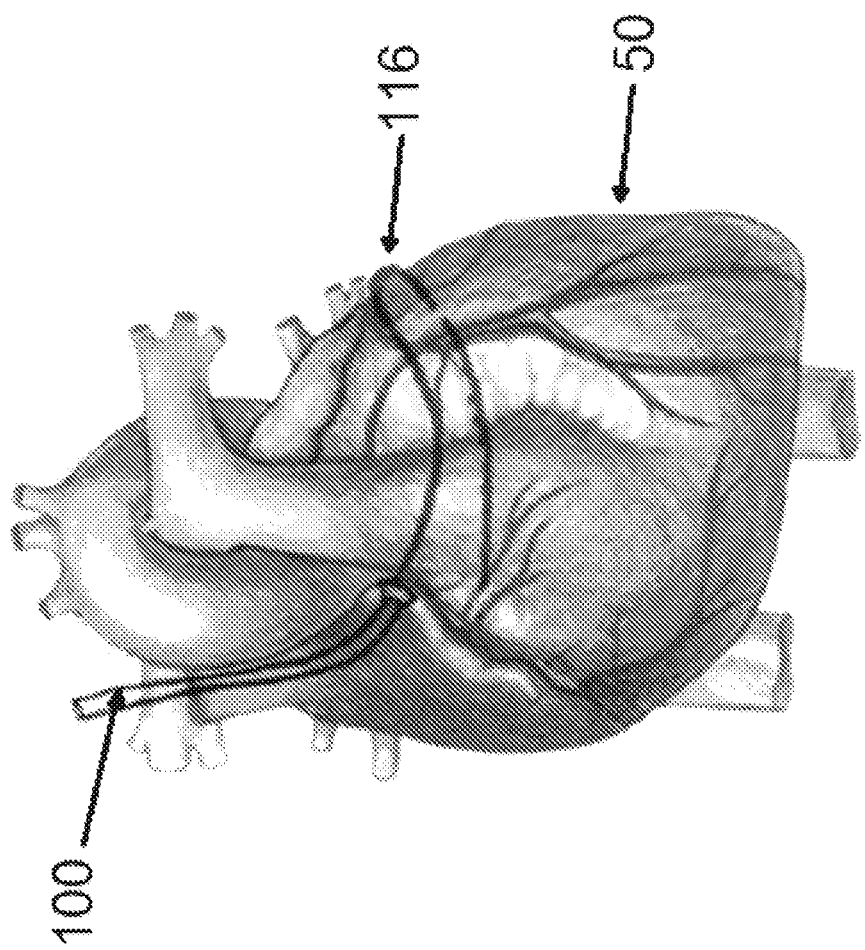
FIG. 1 shows a portion of an outer catheter and a guidewire positioned within or near a mammalian heart, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

The present disclosure includes disclosure of devices, systems and methods for localized delivery of substances into areas within or adjacent to a heart. In at least some embodiments of the present disclosure, said substances, which may include various drugs and/or biopolymers, may be delivered at or near the epicardium of the heart.

FIG. 1 shows an initial view of a portion of an exemplary system 100 (also referred to as a catheter system 100) of the present disclosure positioned within a luminal organ 50 (such as a mammalian heart). A preformed guidewire 116, as referenced in further detail herein, may be advanced percutaneously and intravascularly through a luminal organ 50, so to facilitate introduction and/or advancement of portions of a catheter system 100 within a mammalian patient.

FIG. 2A shows a side view of various components of an exemplary catheter system 100 of the present disclosure. As shown in FIG. 2A, catheter system 100 comprises an outer catheter 102 comprising an elongate body 104 defining a guidewire lumen 106 extending from a device proximal portion 108 to a device distal portion 110. Guidewire lumen 106, as shown in FIG. 2A, has a proximal opening 112 and a distal opening 114, with said openings 112, 114 configured to receive a preformed guidewire 116 therethrough.

In at least one embodiment, and as shown in FIG. 2A, guidewire lumen 106 is defined at or near a relative perimeter of elongate body 104, terminating at a tapered device distal portion 110. Such an embodiment then defines a tapered guidewire lumen 106, as shown in FIG. 2A, so that a relatively proximal portion 118 of guidewire lumen 106 follows a general longitudinal axis (A-A', as shown in FIG. 2A), and so that a relatively distal portion 120 of guidewire lumen 106 follows tapered portion 122 of elongate body 104. As shown in FIG. 2A, and as generally referenced above in connection with FIG. 1, a preformed guidewire 116 (or a portion thereof) may be inserted into proximal opening 112, advanced through guidewire lumen 106, and extended out of distal opening 114 so that a portion of guidewire 116 is exposed distal to distal opening 114.

Outer catheter 102, as shown in FIG. 2A, further defines a central lumen 124 extending along a longitudinal axis (A-A') and configured to slidably receive an inner delivery device 126. Inner delivery device 126, as shown in FIG. 2A, is configured (as referenced in further detail herein) to contain a substance 136 for delivery into a mammalian luminal organ 50 (or into a tissue and/or a space adjacent thereto) while a portion of outer catheter 102 is reversibly stabilized within the mammalian luminal organ 50.

Stabilization can occur in at least three ways, depending on the configuration/componentry of outer catheter 102. In at least one embodiment, and as shown in FIG. 2A, outer catheter 102 is configured to be stabilized within a mammalian luminal organ 50 (such as a heart, blood vessel, or other luminal organ) by way of one or more balloons 128 or a series of balloons 128 (such as a balloon group 400, referenced below). Outer catheter 102 embodiments having one or more balloons 128, or a balloon group 400 as referenced in further detail herein, would further comprise a balloon chamber 130 at or near a device distal portion 110 of outer catheter 102. Balloon chamber 130, in various embodiments, houses balloon(s) 128 or balloon group 400, whereby balloon(s) 128, or balloons of a balloon group 400, may be inflated by way of inflation tube 132 either positioned or defined within, or external to, outer catheter 102. Inflation tube 132, in various embodiments, may be (i) configured as a separate tube (having its own outer wall) within or near central lumen 124, (ii) positioned within a portion of elongate body 104 itself (such as within a wall or lumen defined within a wall of elongate body 104), (iii) positioned external to elongate body 104, and optionally coupled to or positioned adjacent to elongate body 104, (iv) defined as a separate lumen within elongate body, without having its own wall(s) separate from elongate body 104 itself, and/or (v) a combination of the foregoing or a different configuration/positioning, wherein the selected configurations/positions are such that inflation tube 132 can be used to transmit a gas, a liquid, and/or another substance therethrough to facilitate inflation and/or deflation of balloon(s) 128 or balloon group 400.

FIG. 2B shows a cross-sectional view of a portion of an exemplary outer catheter 102 of the present disclosure. As shown therein, outer catheter 102 comprises an elongate body 104 having a guidewire lumen 106 and a central lumen 124 defined therein. In at least one embodiment, the guidewire lumen 106 has a smaller cross-section than the cross-section of central lumen 124. In at least an additional embodiment, and as referenced herein to an embodiment of a catheter system 100 that utilizes suction to stabilize portions of catheter system 100 within a luminal organ of a patient, elongate body 104 further comprises an inflation tube 132 present or defined therein, as shown in FIG. 2B.

Guidewire 116, in various embodiments, may be "preformed," in that various guidewire 116 embodiments may have different shapes, curvatures, bends, kinks, etc., which may correspond to measurements obtained of the transversal heart diameter at the base of the heart, for example. In various embodiments, portions of catheter system 100 (such as outer catheter 102 and/or inner delivery device 126, for example) can follow the preformed guidewire 116 to navigate different target areas of the heart 50. Such a preformed guidewire 116 is novel as it allows a user of catheter system 100 to encircle various diameters of the heart 50 (which were previously measured using by echocardiography, cardiovascular magnetic resonance (CMR), nuclear magnetic resonance (NMR), computed tomography (CT), or potentially another scanning method, as referenced further herein), allowing navigation of outer catheter 102, inner delivery device 126, and/or other components of catheter system 100 mounted over guidewire 116 to be directed to reach different targeted areas of the heart 50 to perform various injection, suction, and/or delivery procedures.

Such preformed guidewires 116 may comprise a number of materials sufficient to allow guidewire 116 to remain preformed even after delivery into a patient, with such materials including, but not limited to, one or more of nitinol, chromium, cadmium, molybdenum, nickel, nickel composite, a nickel titanium alloy, a nickel cadmium alloy, a nickel chromium alloy, a nitinol palladium alloy, a palladium cobalt alloy, platinum, other temperature-memory materials, combinations of the same, and the like. Outer catheter 102 and inner delivery device 126, in various embodiments, may comprise any number of biologically compatible materials, such as various plastics and/or polymers, including, but not limited to, polyurethane and Teflon.

Figure 4:
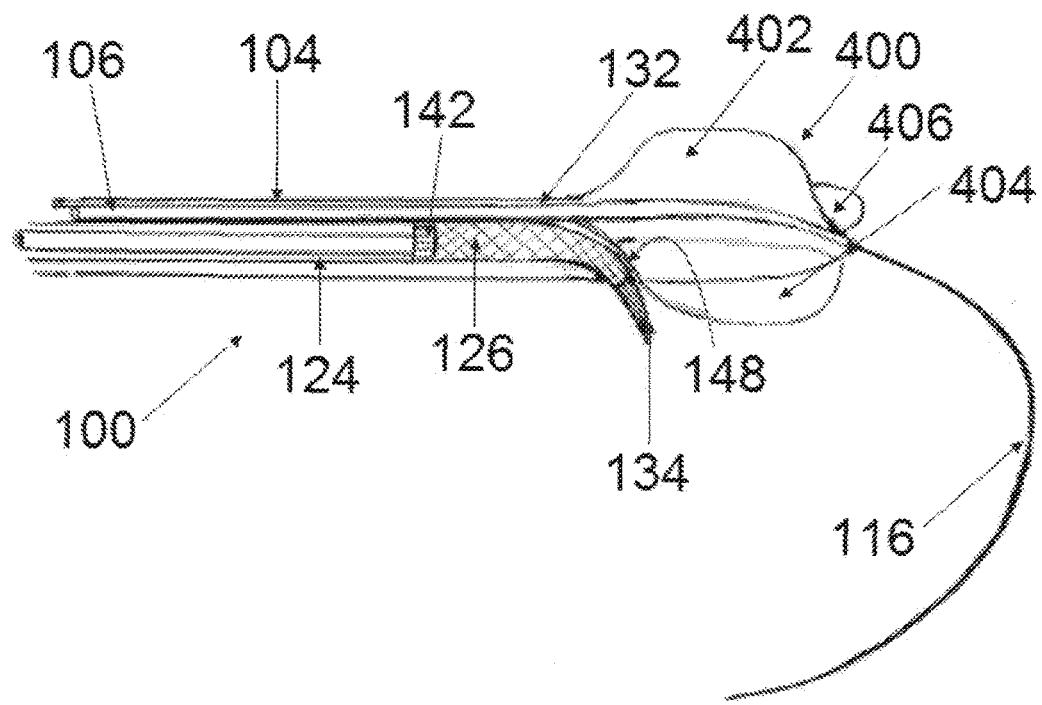
FIG. 4 shows a side cut-away view of a catheter system having a balloon group, according to an exemplary embodiment of the present disclosure.

Balloon 128, or a series of balloons 128 (such as a balloon group 400, referenced below), may be inflated by way of entry of a gas, a liquid, and/or another substance may enter inflation tube 132 to inflate balloon 128 or to inflate a balloon group 400. Balloon group 400, in at least one embodiment and as shown in FIG. 4, may comprise a central compliance balloon 402, a first lateral balloon 404, and a second lateral balloon 406. Upon insertion of outer catheter 102 into a mammalian body (such as through a mammalian luminal organ, by way of advancement of a portion of outer catheter 102 into and through a blood vessel, such as a vein) and inflation of balloon 128 or balloon group 400, the inflated balloon 128 or balloon group 400 temporarily anchors delivery catheter outer catheter 102 in place so that, for example, a substance 136 can be injected within or adjacent to a mammalian luminal organ or potentially removed from the mammalian luminal organ 50 or area adjacent thereto.

Figure 5A:
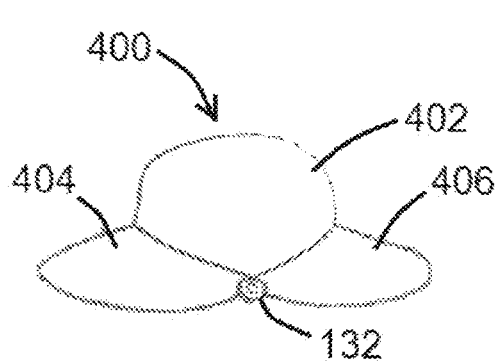
FIG. 5A shows a front view of a balloon group, according to an exemplary embodiment of the present disclosure.
Figure 5B:
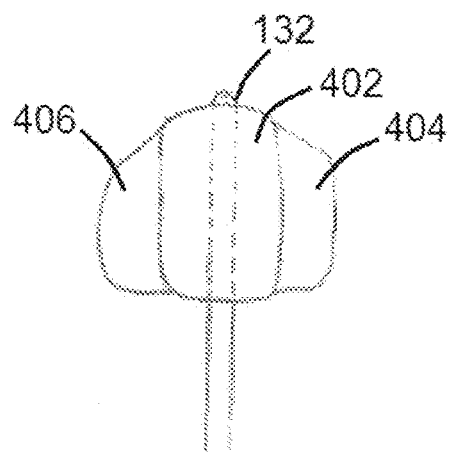
FIG. 5B shows a top view of a balloon group, according to an exemplary embodiment of the present disclosure.

Exemplary embodiments of balloon groups 400 of the present disclosure are shown in FIGS. 5A and 5B. In FIGS. 5A and 5B, balloon groups 400 are coupled to inflation tube(s) 132, with a front view shown in FIG. 5A and a top view shown in FIG. 5B. In each embodiment shown in FIGS. 5A and 5B, balloon groups 400 comprise a central compliance balloon 402, a first lateral balloon 404, and a second lateral balloon 406. Such an exemplary arrangement of balloons within balloon group 400 may optimally assist to anchor outer catheter 102 in place while minimizing stresses to the tissues surrounding balloon group 400. In at least one embodiment, inflation of balloon group 400 causes balloon group 400 to exert pressure against a blood vessel or a luminal organ, including the heart.

Procedurally, portions of catheter system 100 may be inserted into a patient, balloon(s) 128 (or balloon group 400) may be inflated to stabilize the outer catheter 102 to a tissue/luminal organ within a patient, substance 136 may be delivered using inner delivery device 126, balloon(s) 128 (or balloon group 400) may be deflated to release outer catheter 102 from the patient, and catheter system 100 may then be withdrawn from the patient.

Figure 3A:
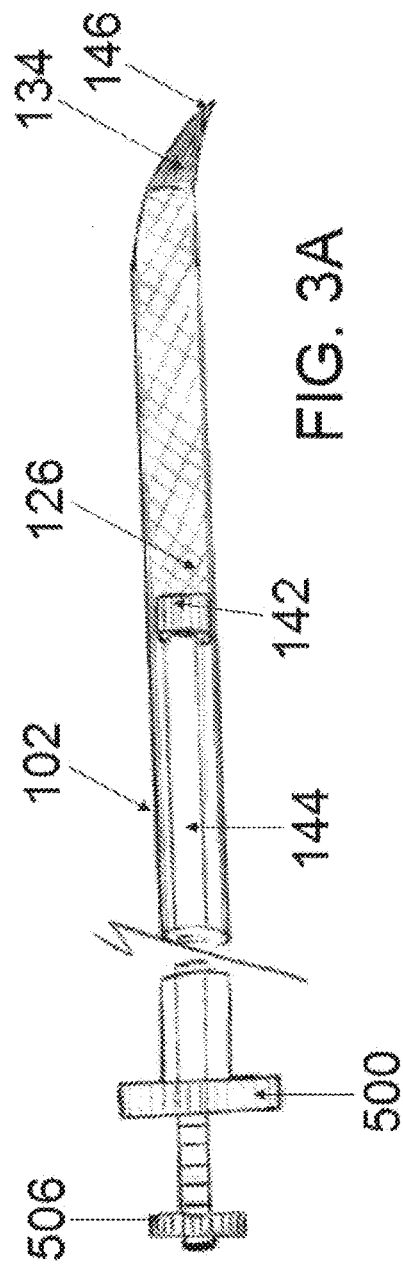
FIGS. 3A and 3B show side cut-away views of inner delivery devices, according to exemplary embodiments of the present disclosure.
Figure 3B:
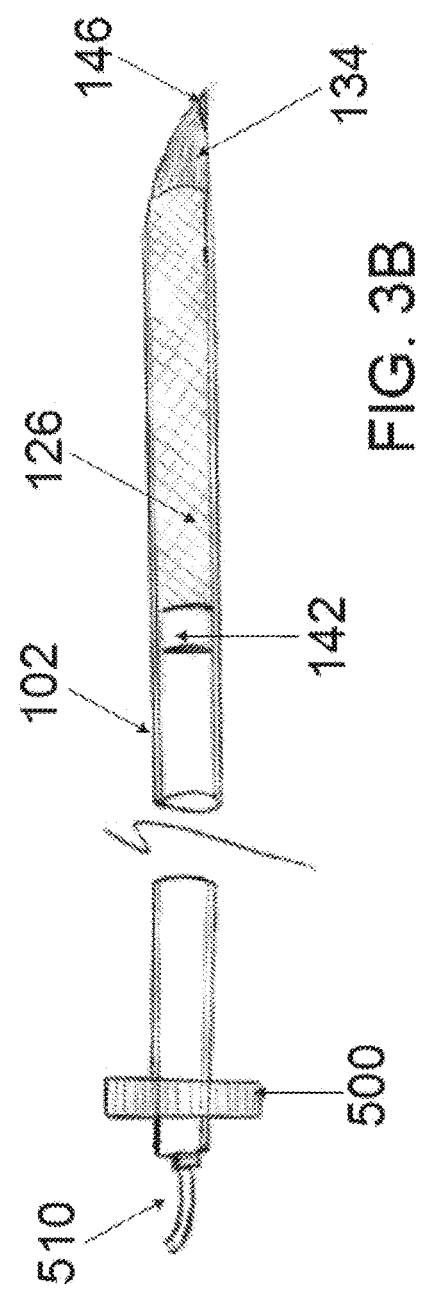

As shown in FIGS. 2A, 3A, and 3B and as referenced above, an exemplary catheter system 100 of the present disclosure comprises an inner delivery device 126 configured to contain a substance for delivery into a mammalian luminal organ 50 (or into a space adjacent thereto) while a portion of outer catheter 102 is reversibly stabilized within the mammalian luminal organ 50. Inner delivery device 126, in various embodiments, comprises a pock tip 134 configured to puncture a mammalian tissue or luminal organ 50, so that a substance 136 (such as a medicament, a polymer, a growth factor, cells (such as myocardial cells), a biological material, or a combination of one or more of the foregoing or another substance intended to be injected into the mammalian tissue, luminal organ, and/or space adjacent thereto) can be delivered from an inner portion 138 of inner delivery device 126, through pock tip 134 (namely through pock tip aperture 146 of pock tip 134), and into the patient. Pock tip 134 of inner delivery device 126, as shown in FIG. 2A, is configured to extend through one or more open channels 140 defined within elongate body 104, wherein the one or more open channels 140 are configured as apertures. Pock tip 134, in various embodiments, may comprise one or more biologically-compatible metals and/or plastics/polymers, whereby said metals, plastics, and/or polymers are sufficiently rigid, and wherein pock tip 134 itself is sufficiently pointed and tapered, so to effectively puncture a tissue or luminal organ 50 and deliver a substance 136 from inner portion 138 of inner delivery device 126 to the patient.

In various embodiments, elongate body 104 of outer catheter 102 defines a plurality of open channels having different angles, such as, for example, 30°, 40°, 60°, and 90° angles, whereby pock tip 134 of inner delivery device 126 can be advanced therethrough to puncture and inject a substance 136 into the cardiac wall, for example. The various angles provide the user of system 100 with options with respect to the angle of substance 136 delivery into a luminal organ 50 or other tissue adjacent to the one or more open channels 140. The angles referenced above, as any number of open channels 140 having angles ranging from just over 0° to just under 180° may be defined within elongate body 104. For example, an exemplary device embodiment may have 30°, 60°, and 90° angles, while another embodiment has 30°, 45°, 60°, and 90° angles.

Figure 6:
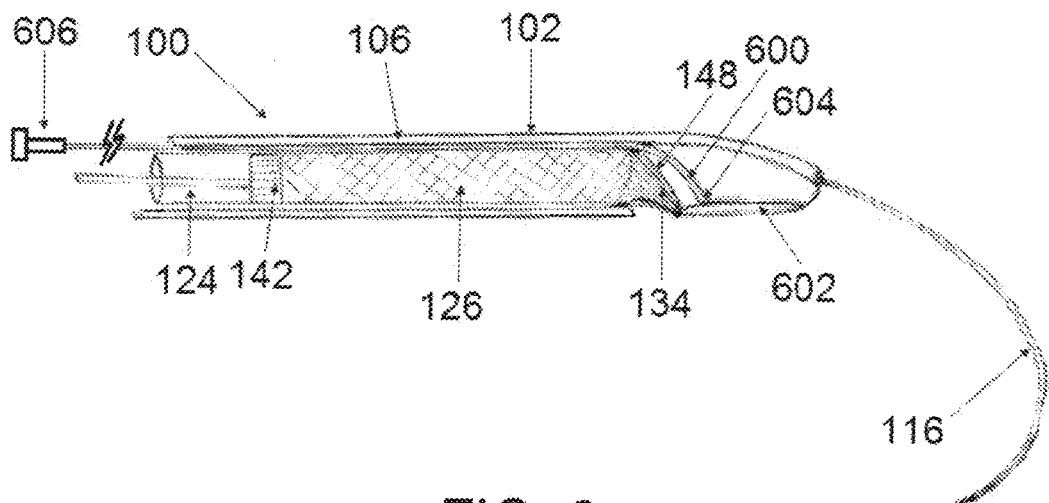
FIG. 6 shows a side cut-away view of a catheter system having a suction chamber, according to an exemplary embodiment of the present disclosure.

Outer catheter 102, as shown in FIG. 2A and in various other embodiments, comprises a pock tip wall 148 defined at or near a relative distal end 150 of inner portion 138. Pock tip wall 148, and in various embodiments, may comprise a complete wall, one or more internal bars, one or more internal protrusions, etc., configured so facilitate the protrusion of a portion of pock tip 134 from an open channel 140. For example, and as shown in FIGS. 2A, 4, and 6, should inner delivery device 126 be fully advanced within central lumen 124 of outer catheter 102, further advancement would cause a portion of pock tip 134 to extend from the only open channel 140 defined therein. As referenced above, pock tip 134 is tapered, with the taper of pock tip 134 corresponding with a taper of pock tip wall 148. Contrary to an end wall that would be perpendicular to a longitudinal axis of an outer catheter, pock tip wall 148, as shown in FIG. 2A for example, would be tapered so that the most distal portion of pock tip wall 148 is adjacent to open channel 140, and so that a relatively proximal portion of pock tip wall 148 is proximal to the most distal portion. Pock tip 134, as shown in the embodiment shown in FIG. 2A, has a corresponding taper to facilitate advancement of a portion of pock tip 134 when pock tip 134 contacts or comes into close proximity to, pock tip wall 148. In at least one embodiment, pock tip 134 and pock tip wall 148 have relatively straight tapers, and in other embodiments, and as shown in FIG. 2A, pock tip 134 and pock tip wall 148 have relatively curved tapers.

Delivery of substance 136, as referenced above, may be facilitated by way of one or more effective actuation methods as shown by way of the various inner delivery device 126 embodiments shown in FIGS. 3A and 3B. As shown in FIGS. 2A, 3A, and 3B, an embolus 142 may be positioned within inner portion 138 of inner delivery device 126, whereby embolus 142 forms an effective barrier to not only facilitate advancement of substance 136 within inner portion 138 toward pock tip 134, but also to prevent substance 136 from leaking/passing proximally to embolus 142. In such an embodiment, for example, if inner portion 138 has a relatively round cross-section, embolus 142 would also have a relatively round cross-section to prevent substance 136 leakage past embolus 142. In addition, and as shown in FIGS. 2A, 3A, 3B, 4, and other figures, inner portion 138 forms an effective container/capsule for substance(s) 136, so that when inner delivery device 126 is advanced into a patient, substance 136 is within inner portion 138 within inner delivery device 126 and is not external to the patient. In such an embodiment, substance 136 may be delivered from an effective container/capsule within the patient directly to the patient, with delivery controlled as further referenced herein.

Embolus 142 may be advanced through inner portion 138 of inner delivery device 126 in a number of ways, including, but not limited to, those shown in FIGS. 3A and 3B. As shown in FIG. 3A, a delivery shaft 144 may be positioned within inner portion 138 of delivery device 126 whereby delivery shaft 144 contacts embolus 142, so that advancement of delivery shaft 144 distally within inner portion 138 facilitates delivery of substance 136 through pock tip aperture 146 and into the patient.

Figure 3C:
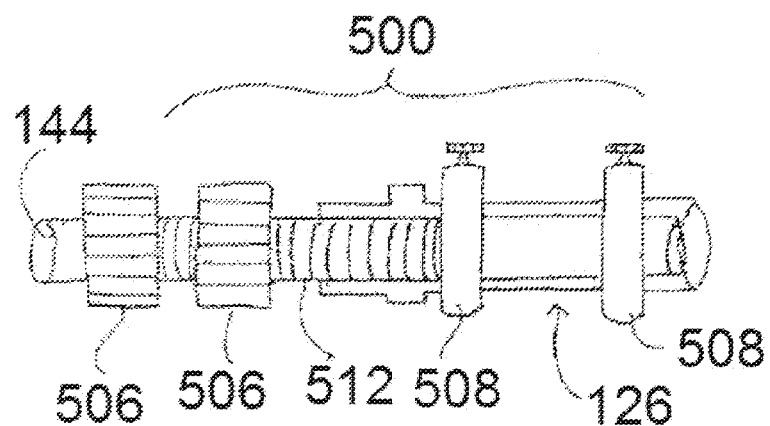
FIGS. 3C and 3D show torque mechanisms coupled to inner delivery devices, according to exemplary embodiments of the present disclosure.
Figure 3D:
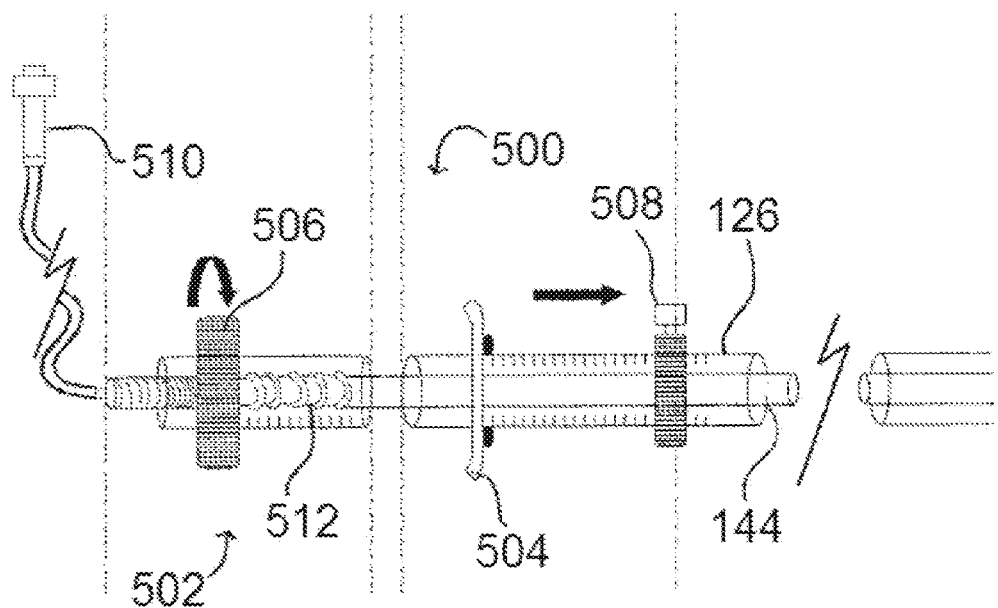

An exemplary catheter system 100 of the present disclosure may comprise a torque mechanism 500 positioned at or near a relative proximal end 502 of inner delivery device 126. Torque mechanisms 500, as shown in FIGS. 3C and 3D, may be coupled to inner delivery device 126, and an optional handle 504 may be coupled to inner delivery device to assist a user to hold the inner delivery device 126 during operation thereof. As shown in FIG. 3D, the proximal end 502 of inner delivery device 126 is coupled with the torque mechanism 500.

Torque mechanisms 500, in various embodiments, comprise at least one rotatable dial 506 operably coupled to, connected to, or engaging delivery shaft 144. In at least one embodiment, the axis of rotatable dial 506 is concentric to the longitudinal axis of delivery shaft 144. Rotatable dial 506 is configured such that the rotatable dial 506 is capable of rotational movement in a direction of a perimeter of inner delivery device 126. Rotatable dial 506 and delivery shaft 144 are configured so that rotational movement of rotatable dial 506 is converted to incremental linear movement of delivery shaft 144.

In at least one embodiment, when the rotatable dial 506 is rotated in a first direction (e.g., clockwise), the delivery shaft 144 is advanced distally within the inner delivery device 126, facilitating delivery of a substance 136 through pock tip 134 and into the patient. Further, and in at least one embodiment, when the rotatable dial 506 is rotated in a second direction (e.g., counterclockwise), the delivery shaft 144 retracts within inner delivery device 126. Rotation in the first direction, as referenced above, can also be used to control the depth of puncture of pock tip 134 into a targeted tissue or luminal organ of the patient.

Certain other embodiments of torque mechanisms 500 of the present disclosure may comprise other types of torque systems, so long as the torque mechanism 500 permits the clinician to reliably advance and optionally retract delivery shaft 144 within inner delivery device. In at least one embodiment, a defined rotation of the rotatable dial 506 (e.g., one full rotation) corresponds to a particular increment that the delivery shaft 144 is advanced or retracted. For example, and in at least one embodiment, one complete clockwise turn of the rotatable dial 506 advances delivery shaft 1 mm. The rotation of the rotatable dial 506 may further be segmented in defined increments such that a user can advance or retract delivery shaft 144 a defined distance without performing a complete rotation of the rotatable dial 506. Further, the torque mechanism 500 can be calibrated by a user to define a specific degree of rotation of the rotatable dial 506 to a precise distance of linear movement. For example, for applications that require a high degree of precision, a user can set torque mechanism to advance/retract the delivery shaft 144 in increments of 0.1 mm per 10 degrees of rotation of the rotatable dial 506. In addition, the segmented increments and/or rotatable dial 506 calibration can be used to measure the amount of substance 136 delivered into the patient. For example, and in at least one embodiment, rotation of rotatable dial one full rotation may correspond to 0.5 mL of substance 136 delivery into the patient. Increments may be indicated on portions of catheter system 100, such as on inner delivery device 126 or outer catheter 102, as indicia 512 as shown in FIGS. 3C and 3D.

Exemplary torque mechanisms 500 of the present disclosure may further comprise at least one limiter 508, which is operatively coupled to the inner delivery device 126. The limiter 508 may be any mechanism capable of preventing the overextension of delivery shaft 144. For example, a clinician can set the limiter 508 to prevent the delivery shaft 144 from advancing more than 8 mm.

In at least another embodiment of a catheter system 100 of the present disclosure, the catheter system 100 has a torque mechanism with a second rotatable dial 506. In such an embodiment, a first rotatable dial 506 can be used, as described above, to control advancement of delivery shaft 144 within inner delivery device 126. In an embodiment with a second rotatable dial 506, the second rotatable dial 506 can also operate consistent with the foregoing, but to instead control advancement of inner delivery device 126 within the central lumen 124 of outer catheter 102. For example, rotation of the second rotatable dial 506 in a first direction can cause inner delivery device 126 to advance distally within central lumen 124, and rotation in a second direction can cause inner delivery device 126 to retract within central lumen 124. As shown in FIG. 3D, an optional second limiter 508 can be used to limit advancement and/or retraction of inner delivery device 126 within central lumen 124.

In other embodiments of torque mechanisms 500 of the present disclosure, and as shown in FIG. 3D, torque mechanism 500 may comprise another manual, mechanical, or compressed air rotatable dial system to measure advancement and/or retraction of various components and/or contents of catheter system 100, as well as the amount of drug/polymer (substance 136) delivery into the patient. For example, and as shown in FIG. 3B, a compressed gas source 510 may be coupled to torque mechanism 500, whereby regulation of the flow of gas from the compressed gas source 510 into catheter system 100 controls movement of embolus 142, which controls the delivery of substance 136. For example, introduction of compressed gas from compressed gas source 510 causes embolus 142 to move distally within inner portion 138 of inner delivery device 126, causing substance 136 to be advanced through pock tip 134 and into the patient.

An additional embodiment of a catheter system 100 of the present disclosure is shown in FIG. 6. As shown in FIG. 6, catheter system 100 comprises a number of similar or the same characteristics of other catheter system 100 embodiments referenced herein, such as an outer catheter 102, an elongate body 104, a guidewire lumen 106, a tapered portion 122 (of elongate body 104), a central lumen 124 (of outer catheter 102), and an inner delivery device 126. Other or fewer components may be used in various other embodiments. However, and as shown in FIG. 6, a different mechanism/configuration is used to stabilize portions of catheter system 100 prior to, during, and/or after injection/delivery of a substance 136 within a mammalian patient, namely suction via one or more suction channels 600 defined along substantially or completely a length of outer catheter 102 and one or more suction chambers 602 at or near a suction channel distal end 604. Suction chamber(s) 602 has/have a larger cross-sectional area than the cross-sectional area of suction channel(s) 600, so that when suction is applied from a suction source 606 (shown in FIG. 6) at or near a proximal end of suction channel(s) 600, the larger cross-sectional area of the suction chamber(s) 602 facilitate, for example, epicardial fixation and stabilization during substance 136 injection. Procedurally, portions of catheter system 100 may be inserted into a patient, suction may be applied to stabilize the outer catheter 102 to a tissue/luminal organ within a patient, substance 136 may be delivered using inner delivery device 126, suction may be ended to release outer catheter 102 from the patient, and catheter system 100 may then be withdrawn from the patient.

Figure 7:
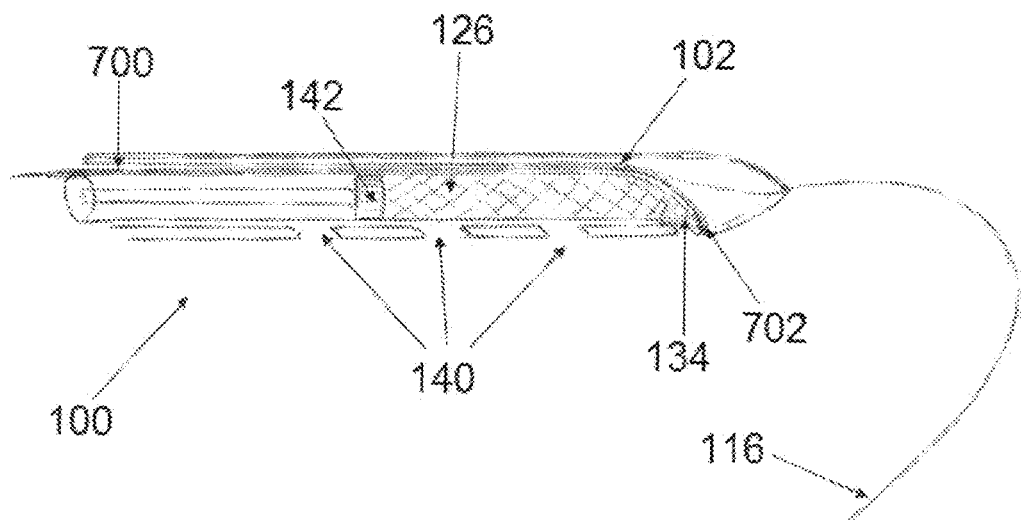
FIG. 7 shows a side cut-away view of a catheter system having multiple open channels, according to an exemplary embodiment of the present disclosure.
Figure 8A:
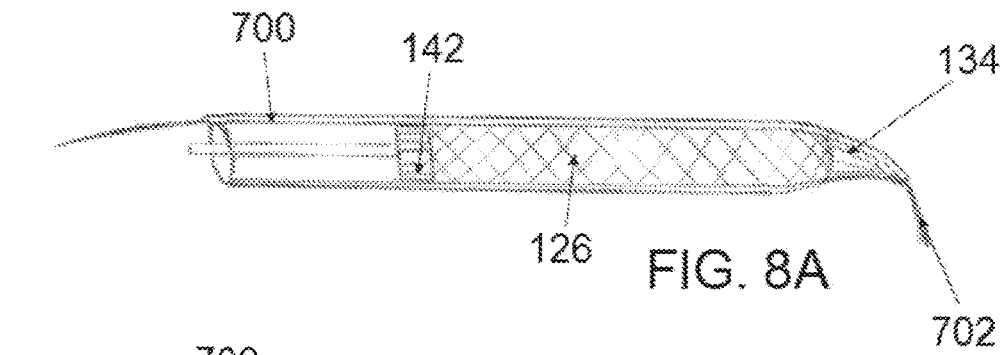
FIG. 8A shows a side cut-away view of an inner delivery device having a needle wire within a needle wire lumen, according to an exemplary embodiment of the present disclosure.
Figure 8B:
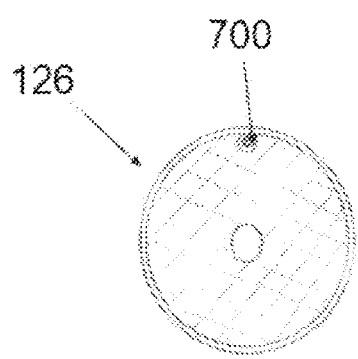
FIG. 8B shows a cross-sectional view of an inner delivery device having a needle wire lumen, according to an exemplary embodiment of the present disclosure.

As shown in FIGS. 7 and 8A, an exemplary inner delivery device 126 of the present disclosure may have a needle wire channel 700 defined therein configured to slidingly receive a needle guidewire 702 therein. Advancement of a portion of needle guidewire 702 through needle wire channel 700 can be performed to puncture an adjacent tissue or luminal organ to facilitate advancement of pock tip 134 into said puncture to deliver substance 136. FIG. 8B shows a cross-sectional view of an exemplary delivery device 126 with needle wire channel 700 defined therein.

Various catheter systems 100 of the present disclosure may be used as follows. If a procedure is used to deliver a substance 136 to the epicardial portion of a heart, the transverse heart diameter at the base may first be measured by echocardiography, cardiovascular magnetic resonance (CMR), nuclear magnetic resonance (NMR), computed tomography (CT), or potentially another scanning method. Based upon said measurement(s), a preformed guidewire 116 of a particular size is selected, and the pericardial sac of the heart is approached using the catheter system 100. A group of guidewires 116 (such as small, medium, and large guidewires 116) may be part of a kit, for example, and depending on the size of the measured transverse heart diameter, a guidewire 116 of the desired size may be used in the procedure. As referenced above, the guidewires 116 may comprise a nickel-titanium alloy (such as nitinol) and/or another temperature-memory material. The selected guidewire 116 would be advanced into a luminal organ of the patient (such as a blood vessel), and the ultimate positioning of a portion of guidewire 116 within the patient may be controlled by fluoroscopy and/or echocardiography (such as, for example, intraoperative epicardial echocardiography (IEE)).

Figure 9:
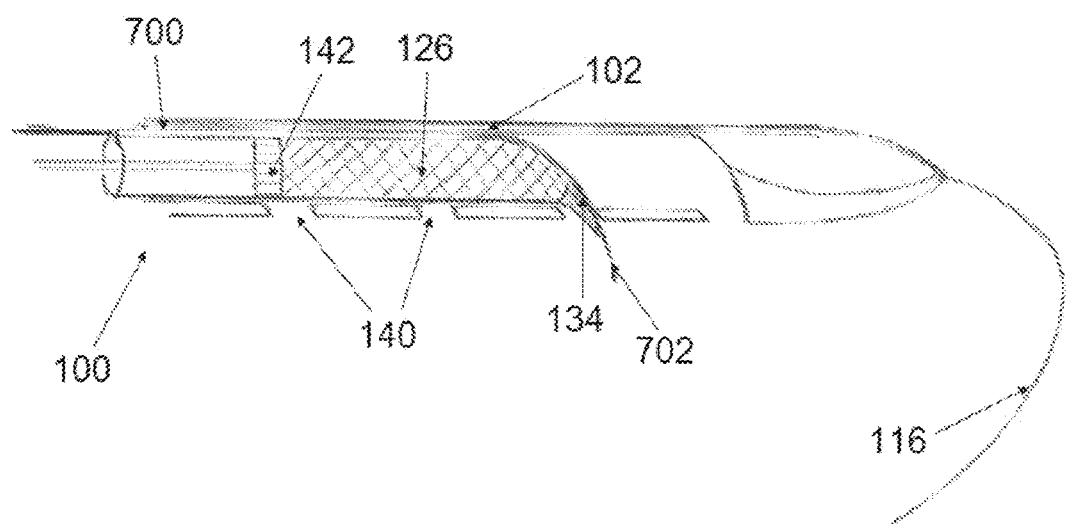
FIG. 9 shows a side cut-away view of a catheter system having multiple open channels, according to an exemplary embodiment of the present disclosure.

After guidewire 116 is positioned as desired, such as shown in FIG. 1, outer catheter 102 may be advanced over guidewire 116 so that guidewire 116 is within guidewire lumen 106. After the device distal portion 110 of outer catheter 102 is positioned at a desired location within the patient's luminal organ, outer catheter 102 can be fixed/stabilized by way of inflation of balloon(s) 128 and/or balloon group 400, or by way of suction through suction channel 600 so that suction chamber 602 reversibly attaches to a tissue at or near the device distal portion. After fixation/stabilization, or prior thereto if desired, internal delivery device 126 may be advanced/slid through central lumen 124 of outer catheter 102, and advancement of the same may be controlled by one or more controlling mechanisms/methods identified above, including, but not limited to manual, mechanical, or air compressed. The inner delivery device 126 may then be used to puncture a tissue or luminal organ, such as the epicardium, and deliver a substance 136 to said tissue or luminal organ. Puncture, in various embodiments, may be performed using pock tip 134, and delivery of substance may be from inner portion 138 and through pock tip aperture 146, with advancement of embolus 142 facilitating said delivery. In embodiments of outer catheters 102 having multiple open channels 140, such as those shown in FIGS. 7 and 9, the delivery procedure can be repeated through one or more other open channels 140, which can allow the user of catheter system 100 to deliver one or more substances 136 at multiple desired locations (namely through the desired open channels 140, whereby the spacings between channels are known). Furthermore, a user of catheter system 100, regardless of the total number of open channels 140, can deliver substance(s) 136 through open channels 140 at different times and/or for different durations as desired. Upon completion of the procedure, fixation/stabilization can be reversed (such as deflation of balloon(s) 128 or balloon group 400, or cessation of suction through suction channel(s) 600), and the catheter system 100 can be removed from the patient.

Several advantages exist in connection with the use of a catheter system 100 embodiments of the present disclosure to deliver a substance 136. As referenced above, such uses involve minimally-invasive procedures which can occur through percutaneous (including percutaneous intravascular) puncture, whereby portions of outer catheter 102 may be easily inserted within said puncture. The outer catheter may be easily positioned following the preformed (memory) guidewire 116. The depth of the puncture for substance 136 delivery, as referenced in various embodiments above, is controlled at the target epicardium (or other bodily tissue or organ) area through the torque mechanism 500, and the injection of the amount(s) of drug/polymer (exemplary substances 136) is/are also controlled by a torque mechanism 500 in embodiments of catheter systems comprising the same. In addition, the drug container internal catheter area (namely the inner portion 138 of inner delivery device 126) allows the possibility of multiple drug/polymer injections with only one inner delivery device 126 and/or one outer catheter 102 insertion. The desired injection pattern, namely the location(s) and duration(s) of injections through one or more open channels, can be prescribed on outer catheter 102 and/or on inner delivery device 126 to ensure deliverability.

As generally referenced herein, various systems 100 of the present disclosure can be used to inject substances 136 at or around the heart. Various substances 136, including those referenced above as well as various other medications, growth factors (such as those used for angiogenesis), cells (such as myocardial cells and other cells), and/or other biological materials can be injected at or around the heart for various purposes. For example, and in addition to the processes referenced herein, various substances 136 can be injected within a pericardial sac, into heart tissue from within the pericardial sac (such as into the epicardium and/or into the myocardium), and/or into other areas of the heart or surrounding the heart using various system 100 embodiments of the present disclosure. Such injections can be used to treat the heart and/or portions within the heart, such as with ventricular remodeling or mitral valve remodeling While various embodiments of devices, systems, and methods for delivering a substance within a mammalian luminal organ or area adjacent thereto have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. An inner delivery device, comprising:
   an inner portion configured to receive a substance therein; and
   a tapered pock tip forming a distal end of the inner delivery device, the pock tip configured to deliver the substance from the inner portion, through a pock tip aperture defined within the pock tip, and into a mammalian tissue and/or luminal organ;
   wherein when the inner delivery device is positioned within an outer catheter having at least one open channel defined therein, the inner delivery device is configured to be advanced within the outer catheter such that the pock tip forming the distal end of the inner delivery device protrudes from the at least one open channel, due to the pock tip being tapered, so to puncture the mammalian tissue and/or luminal organ.

2. The inner delivery device of claim 1, further comprising:
   an embolus positioned within the inner portion, the embolus configured so that the substance remains distal to the embolus when the substance is positioned within the inner portion.

3. The inner delivery device of claim 2, further comprising:
   a delivery shaft positioned proximal to the embolus, the delivery shaft configured to fit within the inner delivery device and facilitate delivery of the substance by way of distal advancement of the embolus within the inner delivery device.

4. The inner delivery device of claim 1, configured to deliver the substance into the mammalian tissue and/or luminal organ or a space adjacent thereto.

5. The inner delivery device of claim 1, wherein the inner delivery device is configured to deliver the substance into the mammalian tissue and/or luminal organ or a space adjacent thereto after the pock tip has punctured the mammalian tissue and/or luminal organ by delivering the substance from the inner portion through the pock tip and into the mammalian tissue and/or luminal organ.

6. The inner delivery device of claim 1, wherein the pock tip comprises a material selected from the group consisting of a biologically-compatible metal and a biologically-compatible plastic/polymer.

7. The inner delivery device of claim 1, wherein the pock tip is rigid.

8. A system, comprising:
   the inner delivery device of claim 1; and
   the outer catheter, comprising:
     an elongate body;
     a guidewire lumen defined within the elongate body and configured to receive at least part of a guidewire therein; and
     a central lumen defined within the elongate body, the central lumen configured to receive at least a portion of the inner delivery device.

9. The system of claim 8, wherein the outer catheter has the at least one open channel defined therein, the at least one open channel configured so that the pock tip can protrude therefrom.

10. The system of claim 8, wherein the outer catheter has a plurality of open channels defined therein, the plurality of open channels configured so that the pock tip can protrude therefrom at different locations along the outer catheter.

11. The system of claim 8, further comprising:
    a handle coupled to the inner delivery device, the handle configured to be held by a user of the inner delivery device during operation of the inner delivery device.

12. The system of claim 8, wherein the outer catheter further comprises:
    a pock tip wall positioned at or near a distal end of the outer catheter, the pock tip wall configured to facilitate protrusion of the pock tip after the pock tip is advanced distally inside the outer catheter to the pock tip wall.

13. A system, comprising:
    an inner delivery device, comprising:
      an inner portion configured to receive a substance therein; and
      a tapered pock tip forming a distal end of the inner delivery device, the pock tip configured to puncture a mammalian tissue and/or luminal organ and to deliver the substance from the inner portion, through a pock tip aperture defined within the pock tip, and into the mammalian tissue and/or luminal organ;
      wherein when the inner delivery device is positioned within an outer catheter having at least one open channel defined therein, the inner delivery device is configured to be advanced within the outer catheter such that the pock tip forming the distal end of the inner delivery device protrudes from the at least one open channel so to puncture the mammalian tissue and/or luminal organ; and
    the outer catheter, comprising:
      an elongate body;
      a guidewire lumen defined within the elongate body and configured to receive at least part of a guidewire therein; and
      a central lumen defined within the elongate body, the central lumen configured to receive at least a portion of the inner delivery device.

14. The system of claim 13, wherein the outer catheter further comprises:
    a pock tip wall positioned at or near a distal end of the outer catheter, the pock tip wall configured to facilitate protrusion of the pock tip after the pock tip is advanced distally inside the outer catheter to the pock tip wall.

15. The system of claim 14, wherein the pock tip wall is tapered toward at least one open channel defined within the outer catheter.

16. The system of claim 15, wherein the tapered pock tip corresponds to the tapered pock tip wall.

17. A method to deliver a substance within a mammalian patient, the method comprising the steps of:

introducing at least part of a system into a mammalian patient, the system comprising an inner delivery device, the inner delivery device comprising:
- an inner portion configured to receive a substance therein; and
- a tapered pock tip forming a distal end of the inner delivery device, the pock tip configured to deliver the substance from the inner portion, through a pock tip aperture defined within the pock tip, and into a mammalian tissue and/or luminal organ;
- wherein when the inner delivery device is positioned within an outer catheter having at least one open channel defined therein, the inner delivery device is configured to be advanced within the outer catheter such that the pock tip forming the distal end of the inner delivery device protrudes from the at least one open channel so to puncture the mammalian tissue and/or luminal organ;

advancing the at least part of the system within the mammalian patient to a targeted tissue or luminal organ; and delivering the substance from within the inner delivery device, through the pock tip of the inner delivery device, and into the targeted tissue or luminal organ.

18. The method of claim 17, wherein the targeted tissue or luminal organ is selected from the group consisting of a pericardial sac, is an epicardial surface of a heart, and a myocardium.

19. The method of claim 17, wherein the delivery of the substance is facilitated by advancement of an embolus and a delivery shaft within the inner delivery device.

* * * * *